(12) United States Patent
Kazarinova et al.

(10) Patent No.: US 6,344,344 B1
(45) Date of Patent: Feb. 5, 2002

(54) METHOD FOR PRODUCING URIDINE-5'-MONOPHOSPHATE BY FERMENTATION USING MUTANT STRAINS OF CORYNEFORM BACTERIA

(75) Inventors: Lyudmila Anatolievna Kazarinova; Vitaliy Arkadievich Livshits; Ekaterina Sergeevna Preobrazhenskaya; Irina Mikhailovna Starovoytova, all of Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/695,409

(22) Filed: Oct. 25, 2000

(30) Foreign Application Priority Data

Oct. 28, 1999 (RU) .......................................... 99122774

(51) Int. Cl.[7] ................................................ C12P 19/38
(52) U.S. Cl. ...................... 435/87; 435/252.3; 435/253; 435/832; 435/836; 435/839
(58) Field of Search ................................ 435/87, 252.3, 435/253, 832, 836, 839

(56) References Cited

FOREIGN PATENT DOCUMENTS

| JP | 57-30476 | 6/1982 |
| JP | 4-158792 | 6/1992 |
| RU | 923186 | 9/1987 |
| RU | 1832127 | 8/1993 |

OTHER PUBLICATIONS

Nudler, A. A., et al., The derepression of Enzymes of—uridine–5–monophosphate and uracil, 1991, FEMS Microbiology Letters, 82:263–266.*

* cited by examiner

*Primary Examiner*—Christopher R. Tate
*Assistant Examiner*—Kailash C. Srivastava
(74) *Attorney, Agent, or Firm*—Oblon, Spivak, McClelland, Maier & Neustadt, P.C.

(57) ABSTRACT

Uridine-5'-monophosphate is produced by cultivating in a nutrient medium an uridine-5'-monophosphate producing mutant of coryneform bacterium and which is characterized by at least a resistance to growth inhibition by pyrimidine analogue or a deficiency in uridine degrading activity or combination of said property by protoplast fusion. This method has the advantage of decreased production of uracil. Thus, uridine-5'-monophosphate can be produced in much greater yields, compared with known methods.

13 Claims, No Drawings

METHOD FOR PRODUCING URIDINE-5'-MONOPHOSPHATE BY FERMENTATION USING MUTANT STRAINS OF CORYNEFORM BACTERIA

TECHNICAL FIELD

The present invention relates to a fermentative method for producing uridine-5'-monophosphate, and to microorganisms for use in such methods.

Uridine-5'-monophosphate is useful as a biochemical reagent or as a starting material for synthesizing pharmaceuticals, see WO 95/16785; EP Patent Specification 0 149 775 B1; US Pat. No. 5,422,343; Clin. Exp. Pharmacol. Physiol. 14(3):253 (1987); and Chim-Pharm. J. (Russia) 27(7):27 (1993).

BACKGROUND ART

Methods of enzymatic production of uridine-5'-monophosphate using uracil and orotic acid as substrates known, so far are described by Agr. Bio 1. Chem. 35:518 (1971) and Biosci. Biotech. Biochem. 61(6):956 (1997).

Known methods for producing uridine-5'-monophosphate by direct fermentative processes include a method using various strains belonging to genus of Streptomyces (Japanese Patent laid-Open Publication No.49-031117) and a method using Micromonosporum resistant to analogues of uracil, uracil ribosides or uracil ribotides, (Japanese Patent laid-Open Publication No.57-018873).

A further process that uses strains of the genus Brevibacterium endowed with a resistance to purine analogues is disclosed in Japanese Patent laid-Open Publication No.57-30476.

A method for producing uridine-5'-monophosphate using strains of Corynebacterium (Brevibacterium) ammoniagenes (hereafter referred to as *Corynebacterium ammoniagenes*) having resistance to pyrimidine analogues is proposed in SU Patent 923186. Yet another later process using strains of *Corynebacterium ammoniagenes* endowed with resistance to pyrimidine analogues is described in Japanese Patent laid-Open Publication No. 4-158792.

A process using strains *Corynebacterium ammoniagenes* obtained from an inosine-5'-monophosphate producer, which strains take on an ability to produce significant amounts of uridine-5'-monophosphate due to sensitivity to the bacteriostatic action of adenine, is proposed in SU Patent 1446927. These strains were characterized by a high resistance to pyrimidine analogues.

Further attempts to increase the productivity of uridine-5'-monophosphate producing strains *Corynebacterium ammoniagenes* by imparting additional properties to them also have been made. For example, it has been found that the productivity of uridine-5'-monophosphate producing strains *Corynebacterium ammoniagenes* can be greatly improved by endowing the adenine-sensitive mutants with resistance to sulfaguanidine, SU Patent 1782028, RU Patent Application 95112366, or to arsenate, SU Patent 1832127. The highest level of uridine-5'-monophosphate accumulation (22.0 g/l) was achieved by using the strain VKPM B-6307 described in RU Patent Application 95112366.

Although the processes exemplified result in improved yields of uridine-5'-monophosphate, from the standpoint of commercial application the production yields of such processes are comparatively low. Thus, a need exists for a process for producing uridine-5'-monophosphate in higher yields at low cost.

A method of producing uridine using a microorganism which belongs to the genus Bacillus, which is deficient in uridine nucleoside phosphorylase activity and which is resistant to pyrimidine analogues, is known, U.S. Pat. No. 4880736. However, it was not known that coryneform bacteria having properties similar to the above microorganism would efficiently produce uridine-5'-monophosphate.

DISCLOSURE OF THE INVENTION

The present invention has been made taking the aforementioned viewpoints into consideration. An object of the present invention is to provide a more efficient method for the production of uridine-5'-monophosphate in high yields for industrial purposes and microorganisms which can be used in such a method.

To this end, the present inventors after many studies on bacteria producing uridine-5'-monophosphate, found that microorganisms belonging to *Corynebacterium ammoniagenes* and having resistance to pyrimidine analogues produce and accumulate a considerable quantity of uridine-5'-monophosphate in a medium. The investigation of a series of mutants showed the direct correlation between resistance to pyrimidine analogues and accumulation of uridine-5'-monophosphate. The higher this resistance: the more the uridine-5'-monophosphate yield. Moreover, it has now been found that certain newly discovered mutants of the known strains, which are resistant to at least one pyrimidine analogue and which are deficient in uridine degrading ability, produce higher yields of uridine-5'-monophosphate and exhibit decreased by-production of uracil than the previously known strains.

Heretofore, it was not recognized that the productivity of uridine-5'-monophosphate could be improved by endowing an uridine-5'-monophosphate producing microorganism with such traits.

Therefore work was continued on the basis of this finding to complete the present invention.

Thus, the present invention is as follows.

(1) Coryneform bacterium which has a resistance to growth inhibition by pyrimidine analogues in a minimal medium containing guanine, arginine and casamino acids, and has an activity to produce uridine-5'-monophosphate.

(2) The bacterium according to (1), wherein the pyrimidine analogue is selected from the group consisting of 6-azauracil, 2-thiouracil, 5-fluorouracil, a riboside thereof or a ribotide thereof.

(3) The bacterium according to (2), wherein the pyrimidine analogues is 5-fluouridine.

(4) The bacterium according to (1), wherein the bacterium belongs to *Corynebacterium ammoniagenes*.

(5) The bacterium according to (4), wherein the bacterium is *Corynebacterium ammoniagenes* LK 40-2 (VKPM B-7811).

(6) A coryneform bacterium which has a resistance to growth inhibition by pyrimidine analogues and has a weaker uridine degrading activity, and has an activity to produce uridine-5'-monophosphate.

(7) The bacterium according to (6), wherein the pyrimidine analogue is selected from the group consisting of 6-azauracil, 2-thiouracil, 5-fluorouracil, a riboside thereof or a ribotide thereof.

(8) The bacterium according to (7), wherein the pyrimidine analogues is 5-fluouridine.

(9) The bacterium according to (6), wherein the bacterium belongs to *Corynebacterium ammoniagenes*.

The bacterium according (9), wherein the bacterium is *Corynebacterium ammoniagenes* LK 75-15 (VKPM B-7812) or LK 75-66 (VKPM B-7813). (11) A method for producing uridine-5'-monophosphate by fermentation comprising the steps of cultivating the bacterium illustrated in any one of above (1) to (10) in a medium to produce and accumulate uridine-5'-monophosphate in the culture, and recovering the uridine-5'-monophosphate therefrom.

The present invention will be explained in detail below.

The microorganisms of the present invention may be obtained from microorganisms inherently having an ability to produce uridine-5'-monophosphate by imparting thereto the specified resistance or the weaker uridine degrading activity.

The term "microorganism which is resistant to a pyrimidine analogue" means a microorganism derived from a strain of bacteria belonging to coryneform bacteria as the parent strain and that has been modified in its genetic properties such that it can grow in medium containing a pyrimidine analogue. The term "pyrimidine analogue" means a substance similar in structure to a pyrimidine base, such as uracil, for example 6-azauracil, 2-thiouracil, 5-hydroxyuracil, 5-fluorouracil, ribosides of these or ribotides of these. It is sufficient that a pyrimidine analogue-resistant microorganism has resistance to one pyrimidine analogue. Usually, a mutant resistant to one type of pyrimidine analogue is resistant to at least one additional pyrimidine analogue.

Thus, as used herein the term "resistant to growth inhibition by pyrimidine analogue" means that mutant is capable of growing in nutrient medium containing pyrimidine analogue as an inhibitor in an amount which would inhibit the grow of the parent strains. As an amount of the inhibitor is concretely exemplified by, for example, more than 100 µg/ml, preferably more than 500 µg/ml.

Similarly, as used herein, the term "weaker uridine degrading activity" means that the mutant cannot utilize uridine as a sole carbon source (uridine-not-utilizing mutant, $UR^{nu}$) unlike the wild type strain. For example, a strain of which uridine nucleoside phosphorylase activity per cell is ½ or less, preferably ⅓ or less than that of a parent strain, alternatively, a strain of which specific activity of uridine nucleoside phosphorylase mesured by the method of C. E. Carter [J. Am. Chem. Soc., 73, 1508–1510 (1951)] is less than 50 nmol·min$^{-1}$·mg$^{-1}$ cell protein has a weaker uridine degrading activity.

The "coryneform bacteria" referred to in the present invention includes bacteria having been hitherto classified into the genus Brevibacterium but united into the genus Corynebacterium at present [Int. J. Syst. Bacteriol., 41, 255 (1981)], and include bacteria belonging to the genus Brevibacterium closely relative to the genus Corynebacterium. Examples of such coryneform bacteria include the followings.

*Corynebacterium ammoniagenes* (*Brevibacterium ammoniagenes*)
*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium* (*Corynebacterium glutamicum*)
*Corynebacterium melassecola*
*Corynebacterium thermoaminogenes*
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Brevibacterium album*
*Brevibacterium cerinum*
*Microbacterium ammoniaphilum*

Specifically, the following strains of these bacteria are exemplified:

*Corynebacterium ammoniagenes* (*Brevibacterium ammoniagenes*) ATCC6871, ATCC6872, VKPM B-6307
*Corynebacterium acetoacidophilum* ATCC13870
*Corynebacterium acetoglutamicum* ATCC15806
*Corynebacterium alkanolyticum* ATCC21511
*Corynebacterium callunae* ATCC15991
*Corynebacterium glutamicum* ATCC13020, 13032, 13060
*Corynebacterium lilium* (*Corynebacterium glutamicum*) ATCC15990
*Corynebacterium melassecola* ATCC17965
*Corynebacterium thermoaminogenes* AJ12340 (FERM BP-1539)
*Corynebacterium herculis* ATCC13868
*Brevibacterium divaricatum* (*Corynebacterium glutamicum*) ATCC14020
*Brevibacterium flavum* (*Corynebacterium glutamicum*) ATCC13826, ATCC14067
*Brevibacterium immariophilum* ATCC14068
*Brevibacterium lactofermentum* (*Corynebacterium glutamicum*) ATCC13665, ATCC13869
*Brevibacterium roseum* ATCC13825
*Brevibacterium saccharolyticum* ATCC14066
*Brevibacterium thiogenitalis* ATCC19240
*Brevibacterium album* ATCC15111
*Brevibacterium cerinum* ATCC15112
*Microbacterium ammoniaphilum* ATCC15354

In addition to the properties already mentioned they may have other specific properties such as various nutrient requirement, drug resistance, drug sensitivity and drug dependence without departing from the scope of the present invention.

The mutant microorganisms useful in carrying out the present invention can be obtained by mutation using conventional mutagenesis such as ultraviolet ray irradiation, X-ray irradiation, radioactive ray irradiation, and a treatment with chemical mutagens followed by the selection by the replica method. The preferred mutagen is N-nitro-N'-methyl-N-nitrosoguanidine (hereafter referred to as NTG).

Thus, it is possible to subject any known strain belonging to coryneform bacteria such as *Corynebacterium ammoniagenes* inherently having an ability to produce uridine-5'-monophosphate to one of the above mutation procedure for obtaining a mutant strain, and then to test the mutant strain to determine whether it satisfies the above-requirement of the present invention concerning resistance to a pyrimidine analogue and uridine degrading activity and it is therefore suitable for use in the invention.

Strains mutated as mentioned above are screened by culturing in a nutrient medium and a strain having the ability to produce uridine-5'-monophosphate in greater yields than its parent strain is selected and used in this invention. Strains satisfying the requirement of the present invention may be obtained also by genetic recombination techniques which are well-known to the person skilled in the art.

Representative examples of the strain to be used in the practice of the invention are *Corynebacterium ammoniagenes* LK 40-2 (VKPM B-7811), LK 75-15 (VKPM B-7812), and LK 75-66 (VKPM B-7813). The coryneform bacteria to be used in producing uridine-5'-monophosphate in accordance with the invention have the same bacteriological properties as the parent strain except for the more resistance to a pyrimidine analogue, weaker uridine degrading activity and ability to produce at higher yields of uridine-5'-monophosphate and decreased by-production of uracil. The deposition numbers (VKPM B-Numbers) are those for the microorganisms which have been internationally deposited in the State Research Institute of Industrial Microorganisms, Russia. These strains, LK 40-2 (VKPM B-7811), LK 75-15 (VKPM B-7812), and LK 75-66 (VKPM B-7813) were deposited in the above depository on Jun. 29, 1999, and transferred from the original deposit to international deposit based on Budapest Treaty on Sep. 1, 2000.

These strains have been derived from *Corynebacterium ammoniagenes* VKPM B-6307 [RU Patent Application 95112366] as the parent strain.

Previously the uridine-5'-monophosphate-producing strain VKPM B-6307 has been obtained from inosine-5'-monophosphate-producing strain *Corynebacterium ammoniagenes* 225-55 (VKPM B-1073) [SU Patent 515783] by sequential introducing into genome of the strain 225-5 of series mutations: sensitivity to adenine, reversion to adenine prototrophy an resistance to sulfaguanidine and arsenate.

As shown in Table 1, parent strain VKPM B-6307 exhibits a complete resistance to all tested pyrimidine analogues even at high concentration unlike the wild type strain *Corynebacterium ammoniagenes* ATCC 6872 under cultivation on basal agar medium A of Table 2.

TABLE 1

The growth of the strains of *Corynebacterium ammoniagenes* in the presence of pyrimidine analogues

| Analogue | Concentration µg/ml | Growth of the strains* ATCC6872 | B-6307 |
|---|---|---|---|
| No addition | 0 | + | + |
| 5-Fluorouracil | 50 | − | + |
|  | 100 | − | + |
|  | 200 | − | + |
|  | 600 | − | + |
| 5-Fluouridine | 100 | − | + |
|  | 200 | − | + |
|  | 400 | − | + |
|  | 600 | − | + |
| 5-Fluorouracil+ | 50+100 | − | + |
| 5-Fluouridine | 100+200 | − | + |
|  | 300+600 | − | + |
| 6-Azauracil or 2-Thiouracil | 500 | − | + |
|  | 1000 | − | + |
|  | 3000 | − | + |
|  | 5000 | − | + |

+: Growth; −: No growth.

TABLE 2

| Composition of medium | Concentration in Medium A | Medium B |
|---|---|---|
| Glucose | 2.0% | 2.0% |
| Urea | 0.2% | 0.2% |
| Ammonium sulfate | 0.3% | 0.3% |
| Potassium dihydrogen phosphate | 0.1% | 0.1% |
| Dipotassium hydrogen phosphate | 0.3% | 0.3% |
| Magnesium sulfate | 0.03% | 0.03% |
| Calcium chloride | 0.01% | 0.01% |
| Manganese chloride | 3.6 mg/l | 3.6 mg/l |
| Ferric sulfate | 10 mg/l | 10 mg/l |
| Zinc sulfate | 1 mg/l | 1 mg/l |
| Thiamine | 5 mg/l | 5 mg/l |
| Calcium pantotenate | 10 mg/l | 10 mg/l |
| Biotin | 30 mg/l | 30 µg/l |
| Guanine | 0 | 100 mg/l |
| Arginine | 0 | 500 mg/l |
| Casamino acid | 0 | 200 mg/l |
| Agar | 2.0% | 2.0% |

This resistance of strain VKPM B-6307 seems to be connected with guanine nucleotides deficiency inherent to all uridine-5'-monophosphate producers, obtaining as adenine sensitive strains, since guanine nucleotides are required for conversion of pyrimidine analogues to the toxic nucleotides.

It has been now found that the strain VKPM B-6307, insensitive to pyrimidine analogues in the absence of guanine, became sensitive to them after the addition of guanine, guanosine or hypoxanthine [Biotechnologia (Russia), 1994, No 7, p.5; J. Bacteriol., 1979, v. 138, No.3, p.731]. Beside, in order to inhibit the synthesis of uridine-5'-monophosphate which can neutralize the inhibiting action of the analogues, it is necessary to add arginine since arginine takes part in the negative control of pyridine biosynthesis. Moreover, the supplementation of medium with amino acids should decrease the ppGpp accumulations, which is known to inhibit uracil phosphoribosyltransferase and thus also decreases the inhibiting action of analogues.

Taking into consideration all above mentioned items the present inventors have worked out the method for selection of uracil analogue resistant mutants from the strains of VKPM B-6307, using special medium B, prepared by adding guanine (100 µg/ml), arginine (500 µg/ml), and casimino acid (200 µg/ml) to basal medium A of Table 2, supplemented by pyrimidine analogues.

As shown in Table 3, the strain VKPM B-6307 is resistant to 5-fluorouracil and 5-fluouridine up to the concentration 1000 µg/ml under cultivation on basal agar medium A of Table 2. However, the addition to this medium of guanine, arginine and casamino acid (medium B) results in loss of resistance and restores the sensitivity of strain VKRM B-6307 to the pyrimidine analogues.

TABLE 3

| 5-Fluorouracil or 5-Fluouridine (µg/ml) | Growth of the strain VKPM B-6307* No addition (medium A) | With addition (medium B) |
|---|---|---|
| 0 | + | + |
| 100 | + | − |
| 200 | + | − |

TABLE 3-continued

| 5-Fluorouracil or 5-Fluouridine ($\mu$g/ml) | Growth of the strain VKPM B-6307* | |
|---|---|---|
| | No addition (medium A) | With addition (medium B) |
| 500 | + | − |
| 1000 | + | − |

*+: Growth; −: No growth.

The parent strain VKPM B-6307 consumed about the half of its pyrimidine biosynthetic potential (in molar expression) on the formation of uracil (the product of uridine-5'-nophosphate degradation). It means that enzymes of this strain participating in sequential two-step uridine-5'-monophosphate degradation to uracil exhibit very high activity. The present inventors have found that mutants with weaker uridine degrading activity produce uridine-5'-monophosphate with a higher yield and with decreased by-production of uracil.

To this end, a suitable mutant may be obtained by using the method of protoplast fusion which can lead to the further improvement of uridine-5'-monophosphate production by combination above-said useful mutations in one strain.

The uridine-5'-monophosphate producing microorganisms obtained in the above manner are cultivated in the same manner as the conventional cultivation of microorganisms. Thus, as the medium, there may be used a liquid culture medium containing a carbon source or sources, a nitrogen source or sources and metal ions and, if necessary, other nutrients such as amino acids, nucleic acid derivatives and vitamins. As the carbon source, for instance, there may be used glucose, fructose, ribose, maltose, mannose, sucrose, starch, starch hydrolyzate, molasses and so forth. As the nitrogen source, there may be used organic nitrogen sources such as pepton, corn steep liquor, soybean meal, yeast extract and urea, and, further, inorganic nitrogen sources such as ammonium salts of sulfuric, nitric, hydrochloric, carbonic and other acids, gaseous ammonia and aqueous ammonia, either singly or in combination. As other nutrients, inorganic salts, amino acids, vitamins and so forth necessary for the bacterial growth are appropriately selected and used either singly or in combination.

The cultivation is generally carried out under aerobic conditions. The medium preferably has a pH within the range of 5 to 9. The cultivation temperature is generally selected within the range of 25° C. to 40° C. so that it may be appropriate for the growth of the microorganisms used and for the accumulation of uridine-5'-monophosphate. The cultivation is preferably conducted until the accumulation of uridine-5'-monophosphate becomes substantially maximal. Generally, 3 to 6 days of cultivation achieves this end.

For the separation and recovery of uridine-5'-monophosphate from the resultant culture broth, there may be used per se known usual techniques of purification.

The method of production of uridine-5'-monophosphate according to the present invention is advantageous from the industrial point of view in that it causes accumulation of uridine-5'-monophosphate in larger amounts with little by-production of uracil.

Best Mode for Carrying Out the Invention

The following examples are intended to illustrate this invention more concretely.

EXAMPLE 1

Corynebacterium ammoniagenes VKPM B-6307 was treated with 50 $\mu$g/ml of NTG for 20 minutes followed by ampicillin-enrichment procedure for obtaining mutants which could not utilize uridine effectively as a sole carbon source (uridine was added into liquid medium A of Table 2 instead of glucose). The obtained mutant cells were plated on a medium B of Table 2 supplemented with guanine (100 $\mu$g/ml), arginine (500 $\mu$g/ml), casamino acids (200 $\mu$g/ml) and 100 $\mu$g/ml of 5-fluorouridine.

The inoculated plates were incubated at 30° C. for 3 days. From among the colonies that had appeared the strain Corynebacterium ammoniagenes LK 40-2 (VKPM B-7811) was selected as a strain capable of growing on medium supplemented with 5-fluourouridine in which the parent strain could not grow.

The extent of resistance to various pyrimidine analogues of this strain as well as that of the parent strain VKPM B-6307 is shown in Table 4.

TABLE 4

| Analogue | Concentration $\mu$g/ml | Growth of the strain* | |
|---|---|---|---|
| | | B-6307 | LK 40-2 |
| No addition | 0 | + | + |
| 5-Fluorouracil | 100 | − | + |
| | 300 | − | + |
| | 500 | − | + |
| | 1000 | − | + |
| 5-Fluouridine | 100 | − | + |
| | 300 | − | + |
| | 500 | − | + |
| | 1000 | − | + |
| 6-Azauracil | 1000 | − | + |
| 2-Thiouracil | 1000 | − | + |

* +: Growth; −: No growth.

The strain Corynebacterium ammoniagenes LK 40-2 was then inoculated into 20 ml main fermentation medium C of Table 5 contained in 250 ml flask, and cultivated with shaking at 34° C. for 5 days. The results are shown in Table 6.

TABLE 5

| Composition of main fermentation medium C | Concentration |
|---|---|
| Glucose | 12.0% |
| Urea | 0.72% |
| Potassium dihydrogen phosphate | 3.0% |
| Magnesium sulfate | 1.0% |
| Calcium chloride | 0.1% |
| Magnesium chloride | 1 mg/l |
| Zinc sulfate | 1 mg/l |
| Ferric sulfate | 10 mg/l |
| Thiamine | 5 mg/l |
| Calcium pantotenate | 10 mg/l |
| Cysteine | 20 mg/l |
| Nicotinic acid | 5 mg/l |
| Biotin | 30 $\mu$g/l |

TABLE 6

| | Accumulation (mg/l) of | |
|---|---|---|
| Strain | Uridine-5'-monophosphate | Uracil |
| VKPM B-6307 | 17.5 | 8.2 |
| LK 40-2 | 21.8 | 4.0 |

EXAMPLE 2

Corynebacterium ammoniagenes VKPM B-6307 was treated with NTG followed by ampicillin-enrichment procedure in the same manner as in Example 1. After such treatment cells were plated on a medium A of Table 2.

Incubation was conducted at 34° C. for 4 days. From among the colonies that had appeared, the mutant strain which could not utilize effectively uridine as a sole carbon source (could not grow on the plates prepared by adding 2.0% of uridine instead of glucose) was selected by the replica plating method. In this way, a strain *Corynebacterium ammoniagenes* LK 75-15 (VKPM B-7812) incapable of growing on this medium (uridine-not-utilizing mutant) was obtained. The parent strain and the mutant (LK 75-15) were compared with respect to uridine nucleoside phosphorylase activity. The uridine nucleoside phosphorylase activity was determined by the method of C. E. Carter [J. Am. Chem. Soc., 1951, v.73, p.1508–1510] is shown in Table 7.

TABLE 7

| Strain | Relative activity of Uridine phosphorylase, % |
| --- | --- |
| VKPM B-6307 | 100 |
| LK 75-15 | 30 |

The extent of resistance to various pyrimidine analogues of these strains is shown in Table 8.

TABLE 8

| | Concentration | Growth of the Strain* | |
| --- | --- | --- | --- |
| Analogue | µg/ml | B-6307 | LK 75-15 |
| No addition | 0 | + | + |
| 5-Fluorouracil | 100 | − | + |
| | 300 | − | − |
| | 500 | − | − |
| | 1000 | − | − |
| 5-Fluouridine | 100 | − | + |
| | 300 | − | + |
| | 500 | − | − |
| | 1000 | − | − |
| 6-Azauracil | 1000 | − | + |
| 2-Thiouracil | 1000 | − | + |

*+: Growth; −: No growth

Cultivation of thus obtained strain *Corynebacterium ammoniagenes* LK-75-15 under the same conditions as used in Example 1, resulted in accumulation 24.0 mg/ml of uridine-5'-monophosphate and 2.8 mg/ml of uracil (Table 9).

TABLE 9

| | Accumulation (mg/ml) | |
| --- | --- | --- |
| Strain | Uridine-5'-monophosphate | Uracil |
| VKPM B-6307 | 17.3 | 8.0 |
| LK 75-15 | 24.0 | 2.8 |

Example 3

The strains which were obtained in above Example 1 and 2, Corynebacterium ammoniagenes LK 40-2 (VKPM B-7811) and LK 75-15 (VKPM B-7812), were used as the parents for the production of the recombinants by protoplast fusion. The genetically marked derivatives of these strains were obtained prior to protoplast fusion.

The strain LK 40-2 was applied to a basal medium A of Table 2 prepared by adding ;100 µg/ml of streptomycin. Incubation was conducted at 34° C. for 4 days. From among the colonies spontaneously appearing on the medium the mutant LK 40-2 Str$^r$ resistant to streptomycin was selected.

The strain LK 75-15 was streaked onto a basal medium A of Table 2 prepared by adding 50 µg/ml of rifampicin and inoculated plates were incubated at 34° C. for 5 days. The mutants LK 75-15 Rif$^r$ resistant to rifampicin was selected from among spontaneously appeared colonies. The selected mutants resistant to streptomycin or rifampicin did not differ notably from the parent strains in their essential properties.

Genetically marked derivatives, LK 40-2 Str$^r$ and LK 75-15 Rif$^r$, were used for protoplast fusion followed by recombinant selection. Protoplasts were formed and fused using the method described by Livshits et al. [Genetika. (Russia), 1982, v.18, No.10, p.1728].

All obtained fusants were tested for their productivity. As a result, *Corynebacterium ammoniagenes* LK 75-66 (VKPM B-7813) was selected as a recombinant strain combining different useful properties of both parent strains and having higher productivity. Strain LK 75-66 was cultivated under the same conditions as those in Example 1, whereupon the uridine-5'-monophosphate accumulation amount to 26.0 mg/ml (Table 10).

TABLE 10

| | Accumulation (mg/ml) | |
| --- | --- | --- |
| Strain | Uridine-5'-monophosphate | Uracil |
| VKPM B-6307 | 17.0 | 7.9 |
| LK 75-66 | 26.0 | 3.4 |

Extent of resistance of this strain to various pyrimidine analogues as well as that of the parent strains LK 40-2 and LK 75-15 is shown in Table 11.

TABLE 11

| | Concentration | Growth of the Strain* | | |
| --- | --- | --- | --- | --- |
| Analogue | µg/ml | LK 40-2 | LK 75-15 | LK 75-66 |
| No addition | 0 | + | + | + |
| 5-Fluorouracil | 100 | + | + | + |
| | 300 | + | − | + |
| | 500 | + | − | − |
| | 1000 | + | − | − |
| 5-Fluouridine | 100 | + | + | + |
| | 300 | + | + | + |
| | 500 | + | − | + |
| | 1000 | + | − | − |
| 6-Azauracil | 1000 | + | + | + |
| 2-Thiouracil | 1000 | + | + | + |

*+: Growth; −: No growth

Example 4

*Corynebacterium ammoniagenes* LK 75-66 was employed as a seed strain. The strain LK 75-66 was cultured with shaking in a seed medium having the next composition: glucose- 2%, yeast extract- 2%, peptone- 1% and sodium chloride- 0.25%. Inoculated medium was incubated at 34° C. for 1 day. Then resulting seed culture was transferred to a jar fermentor of 1.2 capacity, which was charged with 0.7 L of sterilized production medium containing: glucose- 5%, amonia sulfate- 0.5%, potassium dihydrogen phosphate- 3.0%, magnesium sulfate-1%, calcium chloride-0.02%, ferric sulfate-20 mg/l, zinc sulfate-2 mg/l, maganese sulfate-2 mg/l, thiamine- 5 mg/l, calcium pantotenate-10 mg/l, nicotinic acid-5 mg/l, and biotine-30 µg/l. Amount of inoculum was 10% of the medium volume. During the cultivation period, 25% (v/v) aqeos ammonia was automatically introduced into fermentor to the medium at pH 7.0. The 70% glucose solution was pumped into fermentor to maintain glucose concentration within the range 1–4%. In the course of the fermentation the amount of oxygen, temperature, pH value, glucose and ammonium concentration were controlled. After 120 h cultivation the amount of uridine-5'-monophosphate accumulated by the strain LK 75-66 was 28.4 mg/ml and that of uracil was 3.1 mg/ml.

What is claimed is:

1. An isolated coryneform bacterium that is resistant to growth inhibition by a pyrimidine analogue and that produces uridine-5'-monophosphate.

2. The bacterium according to claim 1, wherein said pyrimidine analogue is selected from the group consisting of 6-azauracil, 2-thiouracil, 5-fluorouracil, a riboside thereof or a ribotide thereof.

3. The bacterium according to claim 2, wherein the pyrimidine analogue is 5-fluouridine.

4. The bacterium according to claim 1, wherein said bacterium belongs to *Corynebacterium ammoniagenes*.

5. The bacterium according to claim 4, wherein the bacterium is *Corynebacterium ammoniagenes* LK 40-2 (VKPM B-7811).

6. A coryneform bacterium that is resistant to growth inhibition by a pyrimidine analogue, has a weak uridine degrading activity, and that produces uridine-5'-monophosphate.

7. The bacterium according to claim 6, wherein said pyrimidine analogue is selected from the group consisting of 6-azauracil, 2-thiouracil, 5-fluorouracil, a riboside thereof or a ribotide thereof.

8. The bacterium according to claim 7, wherein the pyrimidine analogue is 5-fluouridine.

9. The bacterium according to claim 6, wherein said bacterium belongs to *Corynebacterium ammoniagenes*.

10. The bacterium according to claim 9, wherein the bacterium is *Corynebacterium ammoniagenes* LK 75-15 (VKPM B-7812) or LK 75-66 (VKPM B-7813).

11. A method for producing uridine-5'-monophosphate by fermentation, comprising the steps of: cultivating the bacterium of claim 1 for a time and under conditions suitable for production of uridine-5'-monophosphate, and recovering the uridine-5'-monophosphate.

12. The method of claim 11, wherein the uridine-5'-monophosphate is recovered from the culture medium.

13. An isolated coryneform bacterium that produces uridine-5'-monophosphate and that is resistant to growth inhibition by a pyrimidine analogue in a minimal medium containing at least 100 mg/L of guanine, 500 mg/L of arginine and 200 mg/L casamino acids.

* * * * *